United States Patent [19]

Bayer

[11] Patent Number: 5,054,735
[45] Date of Patent: Oct. 8, 1991

[54] ACTIVE-SUBSTANCE SUPPORT FOR BEEHIVES

[75] Inventor: Michael Bayer, Cologne, Fed. Rep. of Germany

[73] Assignee: Bayer Aktiengesellschaft, Leverkusen, Fed. Rep. of Germany

[21] Appl. No.: 534,804

[22] Filed: Jun. 7, 1990

[30] Foreign Application Priority Data

Jun. 21, 1989 [DE] Fed. Rep. of Germany ... 8907584[U]

[51] Int. Cl.⁵ .............................................. A01N 25/00
[52] U.S. Cl. .................................. 248/215; 248/301; 248/339; 119/156; 449/3
[58] Field of Search ............... 248/690, 692, 215, 301, 248/304, 307, 308, 317, 323, 327, 339, 340; 106/15.05; 424/411; 119/156; 43/114–116, 136; 449/2–3, 20, 22

[56] References Cited

U.S. PATENT DOCUMENTS

| | | | |
|---|---|---|---|
| 393,062 | 11/1888 | Fay | 248/301 |
| 2,305,426 | 12/1942 | Howell | 248/317 |
| 3,120,345 | 2/1964 | Bolger | 43/116 |
| 3,692,269 | 9/1972 | Hales | 248/339 |
| 4,546,943 | 10/1985 | Fast | 248/339 |
| 4,579,085 | 4/1986 | McGuire | 119/156 |

FOREIGN PATENT DOCUMENTS

| | | |
|---|---|---|
| 890370 | 1/1982 | Belgium . |
| 224697 | 6/1987 | European Pat. Off. . |
| 3427330 | 2/1985 | Fed. Rep. of Germany . |
| 3538265 | 4/1987 | Fed. Rep. of Germany . |
| 3538688 | 5/1987 | Fed. Rep. of Germany . |

Primary Examiner—Ramon O. Ramirez
Assistant Examiner—Robert A. Olson
Attorney, Agent, or Firm—Sprung Horn Kramer & Woods

[57] ABSTRACT

The active-substance support consists of a rectangular film or sheet (1) of a thermoplastic material which, at its upper end, comprises a T-shaped head piece (2) of which the symmetrically arranged hook-like side arms (3,4) can be bent downwards at a right angle along folding lines (5,6) extending parallel to the longitudinal direction. When needed, the initially flat side arms (3,4) are bent downwards at a right angle and hung on the honeycomb frame so that the active-substance strip (1) is kept centrally suspended in a honeycomb passage.

3 Claims, 1 Drawing Sheet

ACTIVE-SUBSTANCE SUPPORT FOR BEEHIVES

BACKGROUND OF THE INVENTION

This invention relates to an active-substance support for beehives in the form of a film or sheet of a thermoplastic material.

In the field of parasite control in bees, there are various known processes for applying the active substance. One possibility is based on the introduction of active-substance supports in the form of plastic strips, sheets or films into the beehives. These sheets or strips are impregnated with a special insecticidal agent and are placed in the honeycomb passages of a beehive in such a way that the bees come into contact with them so that the active substance is transferred. The active substance supports should be positioned centrally between two honeycombs to minimize contact and the possibilities of transfer to the wax and honey.

Hitherto, support strips cut rectangularly from a plastic film had to be fixed in the beehive by means of suitable auxiliary fastenings (cf. for example DE 35 38 688).

SUMMARY OF THE INVENTION

The problem addressed by the invention is to provide a simple, inexpensive and user-friendly active-substance support for beehives which can be introduced into and positioned in the honeycomb passages rapidly and, in regard to position, reproducibly.

According to the invention, this problem is solved by the fact that, at its upper end, the strip-like support is connected to a T-shaped head piece of which the symmetrically arranged hook-like side arms can be bent downwards at a right angle along folding lines extending parallel to the longitudinal direction. The thickness of the strip-like support is advantageously from 0.5 to 2 mm.

The support preferably has an H-shaped opening so that flaps are formed and can be inserted into the corresponding openings of a second support. In this way, two support strips can be joined hanging from one another to form a relatively long strip so that, even with two-tier beehives, the active-substance support may readily be introduced into the lower hive.

The following advantages are afforded by the invention:

the production of the supports is economical by virtue of their machine-friendly shape and may be carried out by injection moulding or stamping;

introduction into the beehive is simple and problem-free and requires no additional fastenings;

since the T-shaped head piece is only unfolded when needed, compact packaging is possible.

One example of an embodiment of the invention is described in detail in the following with reference to the accompanying drawing.

BRIEF DESCRIPTION OF THE DRAWING

The drawing is a plan view of the active-substance support.

DETAILED DESCRIPTION OF THE INVENTION

Figure 1:
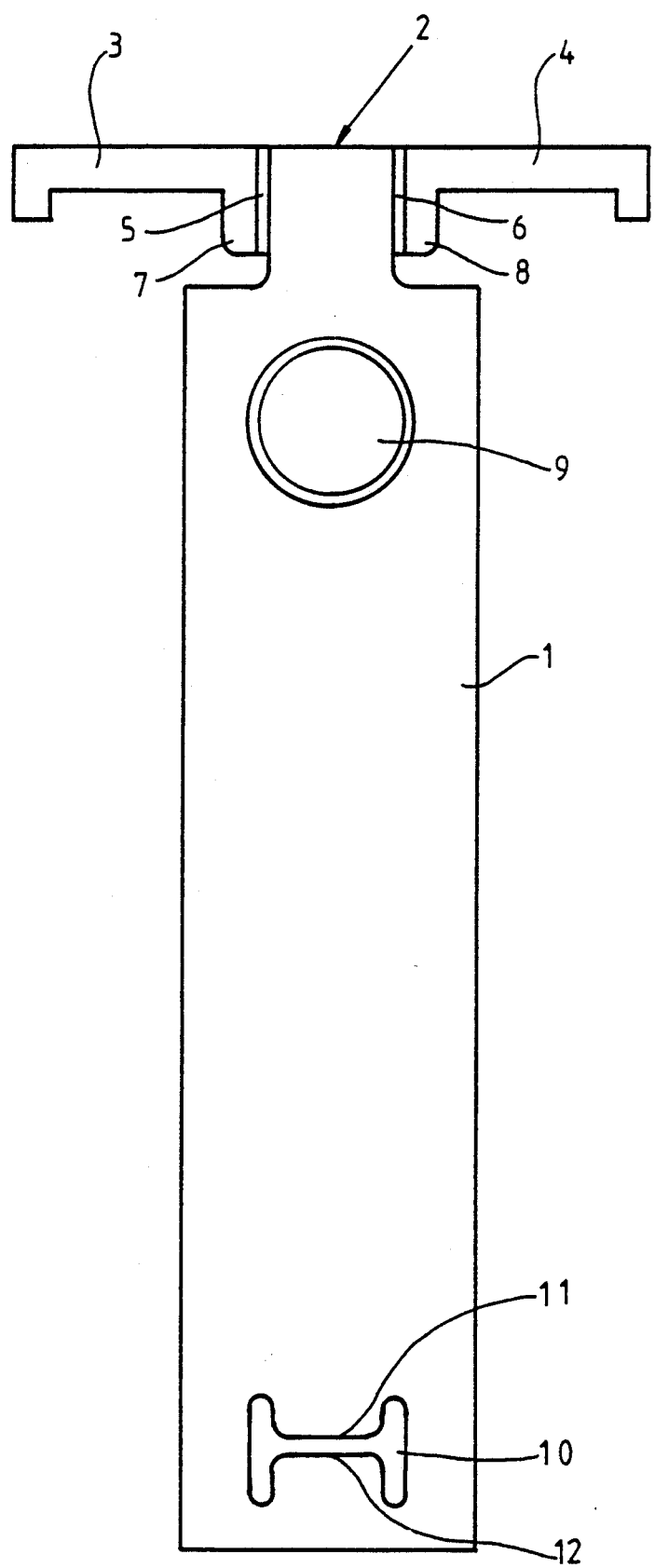

The support consists of a strip-like plastic sheet 1 or film with a T-shaped head piece 2 attached to its upper end. The sheet 1 has a thickness of approximately 1 mm. The head piece 2 consists of two hook-like side arms 3 and 4 which can be bent downwards at a right angle (i.e. out of the plane of the paper) along the folding lines 5 and 6 which extend parallel to the longitudinal direction. The folding lines 5 and 6 are formed by groove-like depressions and act as hinges. When needed, the initially flat side arms 3 and 4 of an active-substance support taken from a supply pack are unfolded and hung on the honeycomb frame so that the active-substance sheet is kept centrally suspended in the particular honeycomb passage. To this end, distance pieces 7 and 8 are provided on the inside of the side arms 3 and 4.

A trade mark 9 or other symbol may be embossed or printed on the active-substance sheet. An H-shaped opening in punched into the active-substance sheet 1 at its lower end so that flaps 11 and 12 are formed and can be folded over perpendicularly of the axis. The opening 10 and the flaps 11 and 12 are used to join two active-substance sheets to one another so that a double-length active-substance support is formed. To this end, the second active-substance sheet is also provided with an H-shaped opening. For this purpose, the two parts are placed over one another so that the H-shaped openings lie over one another and one of the flaps 11,12 is inserted into and hooked in the slot arranged perpendicularly of the axis in the opposite second sheet, so that the two sheets are fixed.

I claim:

1. An active-substance support for beehives comprising a rectangular substrate of a thermoplastic material, a T-shaped head piece connected to an upper end of the substrate and having symmetrically arranged hook-like side arms extending perpendicularly to a longitudinal direction of the substrate and bendable at a right angle to the substrate along folding lines extending parallel to the longitudinal direction of the substrate.

2. An active-substance support as claimed in claim 1, wherein the thickness of the active-substance substrate is 0.5 to 2 mm.

3. An active-substance support as claimed in claim 1, wherein the substrate has an H-shaped opening at a lower end thereof for receiving the head piece of another support sheet to connect the two in series.

* * * * *